(12) United States Patent
Hirabayashi et al.

(10) Patent No.: US 9,024,512 B2
(45) Date of Patent: May 5, 2015

(54) RESONANT TRANSDUCER, METHOD OF PRODUCING THE RESONANT TRANSDUCER, AND ULTRASONIC TREATMENT TOOL INCLUDING THE RESONANT TRANSDUCER

(75) Inventors: Yasutoshi Hirabayashi, Kanagawa (JP); Takamichi Fujii, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 579 days.

(21) Appl. No.: 13/366,130

(22) Filed: Feb. 3, 2012

(65) Prior Publication Data

US 2012/0221029 A1   Aug. 30, 2012

(30) Foreign Application Priority Data

Feb. 28, 2011   (JP) ................. 2011-042511

(51) Int. Cl.
| | | |
|---|---|---|
| *H01L 41/09* | (2006.01) | |
| *A61B 17/32* | (2006.01) | |
| *A61B 17/22* | (2006.01) | |
| *H01L 41/08* | (2006.01) | |
| *H01L 41/316* | (2013.01) | |
| *H01L 41/25* | (2013.01) | |
| *A61B 17/00* | (2006.01) | |

(52) U.S. Cl.
CPC ..... *A61B 17/320036* (2013.01); *A61B 17/2202* (2013.01); *H01L 41/081* (2013.01); *H01L 41/25* (2013.01); *H01L 41/316* (2013.01); *A61B 2017/00526* (2013.01)

(58) Field of Classification Search
USPC ................................. 310/320, 346
See application file for complete search history.

(56) References Cited

U.S. PATENT DOCUMENTS

| | | | |
|---|---|---|---|
| 8,304,966 B2* | 11/2012 | Suenaga et al. ............... | 310/358 |
| 8,633,635 B1* | 1/2014 | Pan .............................. | 310/346 |
| 2004/0175585 A1* | 9/2004 | Zou et al. ..................... | 428/469 |
| 2010/0091073 A1* | 4/2010 | Nihei ............................ | 347/68 |
| 2010/0156247 A1* | 6/2010 | Shibata et al. ............... | 310/346 |
| 2011/0101828 A1 | 5/2011 | Noda et al. | |
| 2012/0212102 A1* | 8/2012 | Hirabayashi et al. ........ | 310/322 |
| 2013/0200752 A1* | 8/2013 | Kuypers et al. ............. | 310/320 |
| 2014/0306580 A1* | 10/2014 | Thalmayr et al. ............ | 310/346 |

FOREIGN PATENT DOCUMENTS

| | | |
|---|---|---|
| JP | 2002-65689 A | 3/2002 |
| JP | 2005-94552 A | 4/2005 |
| WO | WO 2009/157189 A1 | 12/2009 |

OTHER PUBLICATIONS

Kurosawa et al.: "Enhancement of Vibration Amplitude of Micro Ultrasonic Scalpel using PZT Film" Technical Report of the Institute of Electronics, Information and Communication Engineers (IEICE), US2009-109(213)31.

* cited by examiner

*Primary Examiner* — Thomas Dougherty
(74) *Attorney, Agent, or Firm* — Birch, Stewart, Kolasch & Birch, LLP (57) ABSTRACT

A resonant transducer comprising:
 a vibration plate; and
 a piezoelectric element including a piezoelectric film and an upper electrode that are laminated on the vibration plate, wherein
 a compressive stress is applied to the piezoelectric film.

6 Claims, 6 Drawing Sheets

RESONANT TRANSDUCER, METHOD OF PRODUCING THE RESONANT TRANSDUCER, AND ULTRASONIC TREATMENT TOOL INCLUDING THE RESONANT TRANSDUCER

BACKGROUND OF THE INVENTION

1. Field of the Invention

The present invention relates to a resonant transducer, a method of producing the resonant transducer, and an ultrasonic treatment tool including the resonant transducer, and more particularly, to a resonant transducer that can achieve a high vibration speed, a method of producing the resonant transducer, and an ultrasonic treatment tool including the resonant transducer.

2. Description of the Related Art

In recent years, an incision site is required to be as small as possible in medical practice in terms of an early recovery after surgery and a reduction in burden on a patient, and endoscopic surgery is actively adopted as the solution. For the endoscopic surgery, various surgical tools have been developed, and the application range thereof is becoming increasingly wider. Under such a circumstance, an ultrasonic knife is expected as one of the tools for endoscopic surgery.

With regard to ultrasonic treatment tools as described above, Japanese Patent Application Laid-Open No. 2002-65689 describes an ultrasonic treatment tool that ultrasonically vibrates a treating part by means of: a piezoelectric element that generates ultrasonic vibration; a horn part that increases the amplitude of the generated ultrasonic vibration; and a probe that transmits the vibration.

In addition, "Enhancement of Vibration Amplitude of Micro Ultrasonic Scalpel using PZT Film", Minoru KUROSAWA and Takeshi SASANUMA, Technical Report of The Institute of Electronics, Information and Communication Engineers (IEICE), US2009-109(213)31 proposes a micro ultrasonic scalpel for use in endoscopic surgery, the micro ultrasonic scalpel using longitudinal vibration (vibration that is substantially perpendicular to the surface of a biological body to be cut). The longitudinal vibration is excited in a $d_{31}$ mode of a piezoelectric film, and a sensor device for detecting the vibration speed can be incorporated.

In the ultrasonic treatment tool described in Japanese Patent Application Laid-Open No. 2002-65689, a bolted Langevin vibrator is used for the piezoelectric element in order to achieve a high vibration speed. Unfortunately, the vibration speed is not high enough to enable the ultrasonic treatment tool to perform incision and clotting, and hence the horn part that increases the vibration speed is necessary. In order to increase the vibration speed by the horn part, however, the size of the vibrating portion needs to be larger than that of the treating part. Accordingly, in consideration of actual use of the ultrasonic treatment tool in an endoscope, the size of the vibrating portion is limited to about 2 mm to 3 mm in diameter, and hence the treating part needs to be smaller than this size, resulting in an increase in treatment time. In addition, "Enhancement of Vibration Amplitude of Micro Ultrasonic Scalpel using PZT Film" describes a rectangular configuration without a horn part and a configuration with a horn part having a transformation ratio of 3.5, and also describes that the vibration speed of the vibrating portion is 2 m/s in the case of the rectangular configuration and is 7 m/s in the case of the configuration with the horn part. In order to enable the ultrasonic treatment tool to perform incision and clotting, the vibration speed of 7 m/s is necessary, and hence the transformation ratio needs to be set to be equal to or more than 3.5. In this case, the width of the treating part is smaller than 1 mm. In addition, the torque of the vibration is reduced in accordance with the transformation ratio, and hence the torque is unfavorably small.

The present invention has been made in view of the above-mentioned circumstances, and therefore has an object to provide a resonant transducer that can achieve a high vibration speed, a method of producing the resonant transducer, and an ultrasonic treatment tool including the resonant transducer.

SUMMARY OF THE INVENTION

In order to achieve the above-mentioned object, the present invention provides a resonant transducer including: a vibration plate; and a piezoelectric element including a piezoelectric film and an upper electrode that are laminated on the vibration plate, in which a compressive stress is applied to the piezoelectric film.

In general, the tensile strength of the piezoelectric film is smaller than the compressive strength thereof, and hence the vibration speed of the resonant transducer is determined depending on the tensile strength. According to the present invention, a compressive stress is applied as an internal stress to the piezoelectric film itself, and hence a tensile stress higher than that in the normal case can be applied to the piezoelectric film. Accordingly, a vibration speed higher than that in the conventional case can be achieved.

In the present invention, it is preferable that the vibrating plate vibrate in an expanding/contracting manner in a direction parallel to a surface on which the piezoelectric element is formed.

According to the present invention, the vibrating plate vibrates in the expanding/contracting manner in the direction parallel to the surface on which the piezoelectric element is formed. Accordingly, in the case where the resonant transducer is applied to an ultrasonic treatment tool, an incision action of a biological body and a hemostatic action with coagulation can be obtained.

In the present invention, it is preferable that the piezoelectric film have a film thickness that is equal to or more than 1 μm and equal to or less than 5 μm.

According to the present invention, the film thickness of the piezoelectric film is set to the above-mentioned range, whereby the apparatus can be downsized.

In the present invention, it is preferable that an internal stress of the piezoelectric film be a compressive stress equal to or more than 100 MPa.

According to the present invention, the internal stress of the piezoelectric film is a compressive stress equal to or more than 100 MPa, and hence the vibration speed of a resonant transducer having a rectangular configuration can be increased up to 3.5 m/s. Accordingly, even if the transformation ratio of the vibration amplifying portion is designed to be equal to or less than 2.0, the vibration speed of the vibrating portion can be equal to or more than 7.0 m/s.

In the present invention, it is preferable that an internal stress of the piezoelectric film be a compressive stress equal to or more than 300 MPa.

According to the present invention, the internal stress of the piezoelectric film is a compressive stress equal to or more than 300 MPa, and hence a vibration speed equal to or more than 7.0 m/s can be obtained in the case of a resonant transducer having a rectangular configuration, leading to a wider range in design. In addition, in the case where the driving portion is provided in a portion to be inserted into a body, of a treatment tool, the drive voltage cannot be high, but according to the present invention, the vibration speed can be enhanced by increasing the drive voltage in a voltage range within which the treatment tool can work safely in the body.

In the present invention, it is preferable that the vibrating plate have surfaces supported only in a direction perpendicular to a vibration direction thereof.

According to the present invention, the vibrating plate has the surfaces supported only in the direction perpendicular to the vibration direction thereof, and hence the vibrating plate can be easily vibrated.

In the present invention, it is preferable that the vibrating plate have a coefficient of thermal expansion larger than a coefficient of thermal expansion of the piezoelectric film.

According to the present invention, the vibrating plate has a coefficient of thermal expansion larger than the coefficient of thermal expansion of the piezoelectric film. Hence, when the temperature is returned to room temperature after film formation at a high temperature, distortion is caused due to a difference in coefficient of thermal expansion therebetween. Accordingly, an internal stress can be applied to the piezoelectric film.

In order to achieve the above-mentioned object, the present invention also provides a method of producing a resonant transducer, including the steps of: forming a piezoelectric film on a vibrating plate at a temperature equal to or higher than 400° C., the piezoelectric film having a coefficient of thermal expansion smaller than a coefficient of thermal expansion of the vibrating plate; and returning temperature of the vibrating plate and the piezoelectric film to room temperature, in which a compressive stress is applied to the piezoelectric film due to a difference in coefficient of thermal expansion between the vibrating plate and the piezoelectric film.

According to the present invention, a material having a coefficient of thermal expansion smaller than that of the vibrating plate is used for the piezoelectric film, and the temperature is returned to room temperature after the film formation at a temperature equal to or more than 400° C., whereby distortion can be caused between the vibrating plate and the piezoelectric film due to a difference in coefficient of thermal expansion. Accordingly, an internal stress can be applied to the piezoelectric film.

In order to achieve the above-mentioned object, the present invention also provides an ultrasonic treatment tool including the resonant transducer described above.

The resonant transducer according to the present invention can achieve a high vibration speed, and hence the vibration amplifying portion is not necessary, or the transformation ratio of the vibration amplifying portion can be smaller, so that the size of the treating part can be larger. Accordingly, the resonant transducer according to the present invention can be suitably applied to the ultrasonic treatment tool.

In the resonant transducer, the method of producing the resonant transducer, and the ultrasonic treatment tool including the resonant transducer according to the present invention, a compressive stress is applied to the piezoelectric film during the formation thereof, whereby a high vibration speed can be achieved.

DETAILED DESCRIPTION OF THE PREFERRED EMBODIMENTS

Hereinafter, embodiments of a resonant transducer and an ultrasonic treatment tool including the resonant transducer according to the present invention are described in detail with reference to the attached drawings.

[Resonant Transducer]

Figure 1A:
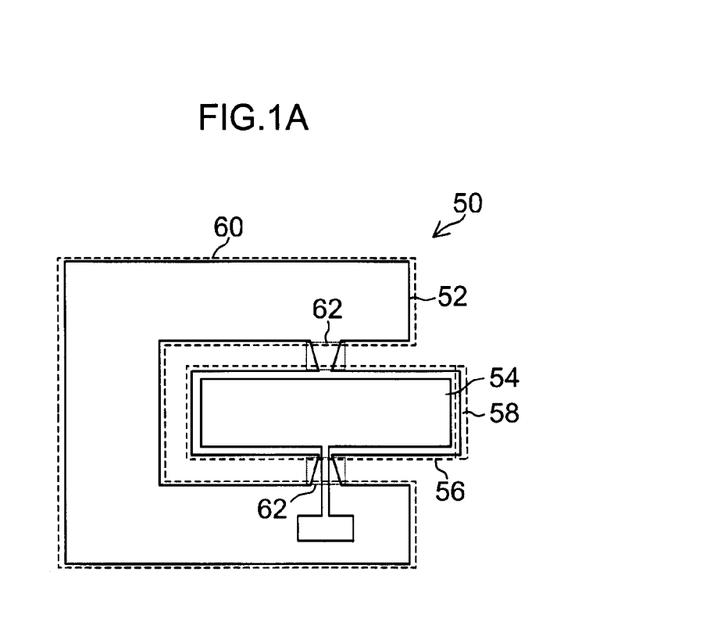
FIGS. 1A and 1B are plan views each illustrating a structure of a resonant transducer.
Figure 1B:
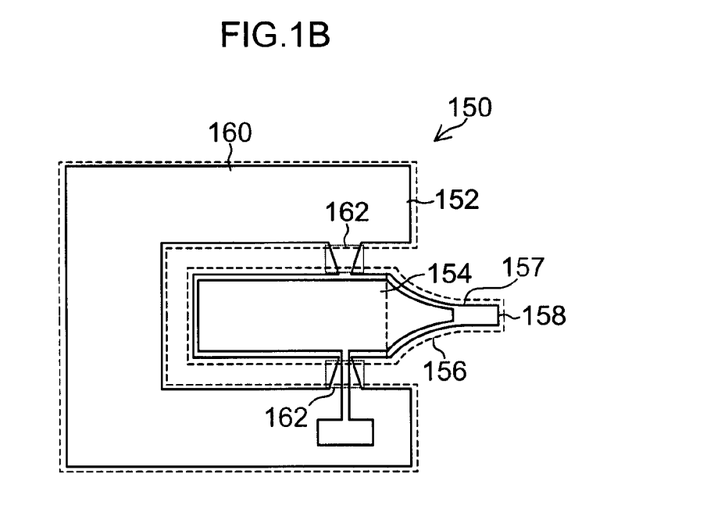

FIG. 1A is a plan view schematically illustrating a structure of a resonant transducer according to a first embodiment of the present invention, and FIG. 1B is a plan view schematically illustrating a structure of a resonant transducer according a second embodiment of the present invention. The resonant transducer according to the second embodiment is different from the resonant transducer according to the first embodiment in that a vibration amplifying portion that increases the vibration speed of a driving portion is provided. Description is given below mainly of the resonant transducer according to the first embodiment. Although the resonant transducer according to the second embodiment is different from the resonant transducer according to the first embodiment in that the vibration amplifying portion is provided, the other configuration of the second embodiment is the same as that of the first embodiment.

Figure 2:
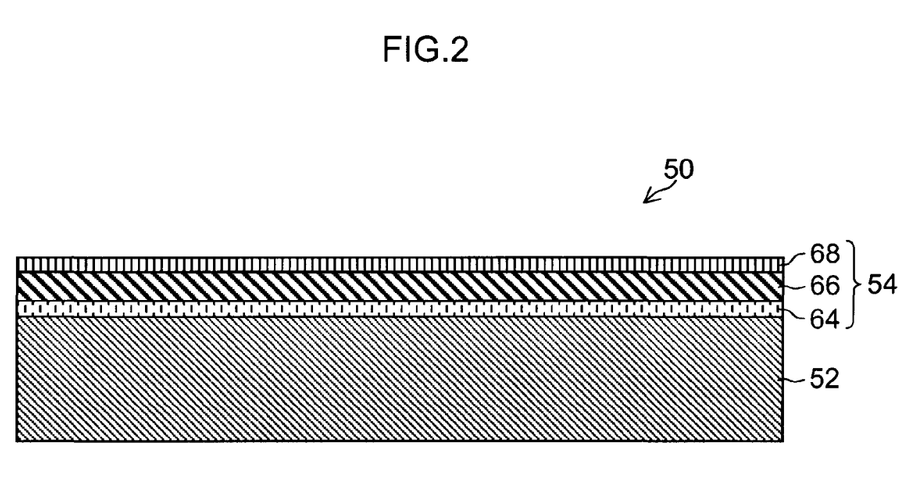
FIG. 2 is a cross-sectional view illustrating a structure of a driving portion of the resonant transducer.

As illustrated in FIGS. 1A and 1B, a resonant transducer 50 includes: a driving portion 56 that includes a piezoelectric element 54 on a substrate 52 and vibrates the substrate 52; a vibrating portion 58 that corresponds to the leading end of the substrate 52 and vibrates by driving of the piezoelectric element 54; a supporting portion 60 that supports the driving; and a fixing portion 62 that fixes the driving portion 56 to the supporting portion 60. The resonant transducer 50 vibrates in the left-right direction of FIG. 1A. Accordingly, it is preferable that the driving portion 56 and the vibrating portion 58 have surfaces that are fixed by the fixing portion 62 to the supporting portion 60 in the direction perpendicular to the vibration direction, that is, in the top-bottom direction of FIG. 1A. In addition, in the second embodiment, a vibration amplifying portion 157 is provided for increasing the vibration speed obtained in a driving portion 156 and transmitting the increased vibration speed to a vibrating portion 158. Note that, as illustrated in FIGS. 1A, 1B and 2, the piezoelectric element 54 is provided on the driving portion 56, the fixing portion 62, and part of the supporting portion 60, and this is because an electrode is to be connected to the piezoelectric element 54 on the supporting portion 60. The position at which the piezoelectric element 54 is formed is not particularly limited as long as the piezoelectric element 54 is formed on the driving portion 56. The transformation ratio of the vibration amplifying portion in the second embodiment can be determined by the length in the width direction of the driving portion, the length in the width direction of the vibrating portion, and the shape of a horn.

[Piezoelectric Element]

Next, the piezoelectric element 54 included in the resonant transducer 50 according to the present invention is described. As illustrated in FIG. 2, the piezoelectric element 54 includes a lower electrode 64, a piezoelectric film 66, and an upper electrode 68 that are laminated on the substrate 52 in the stated order. An electric field is applied to the piezoelectric film 66 by the lower electrode 64 and the upper electrode 68 in the thickness direction of the piezoelectric element 54. When the electric field is applied, the piezoelectric film 66 expands/contracts in the direction ($d_{31}$ direction) perpendicular to the electric field direction of the piezoelectric element 54, so that the structure vibrates in an expanding/contracting manner in the longitudinal direction of the substrate 52, that is, in the direction parallel to the surface of the substrate 52 on which the piezoelectric element 54 is formed.

Examples of the material of the substrate 52 include Ti, Al, SUS, and alloys thereof. It is preferable to use a substrate having a coefficient of thermal expansion larger than the coefficient of thermal expansion of the piezoelectric film such that a compressive stress is applied to the piezoelectric film owing to the relation between the substrate and the piezoelectric film. It is particularly preferable to use Ti and alloys thereof. In the case of using Ti and the alloys thereof, a compressive stress can be easily applied to the piezoelectric film owing to the relation in the coefficient of thermal expansion. In addition, Ti and the alloys thereof can be safely used for the ultrasonic treatment tool to be described later or other such tools.

The lower electrode 64 can be provided as needed. For example, in the case where the substrate 52 is made of an electrically conductive material such as metal, the piezoelectric film 66 can be formed directly on the substrate 52 without providing the lower electrode. The main component of the lower electrode 64 is not particularly limited, and examples thereof include: metal or metal oxides such as Au, Pt, Ir, $IrO_2$, $RuO_2$, $LaNiO_3$, and $SrRuO_3$; and combinations thereof. The main component of the upper electrode 68 is not particularly limited, and examples thereof include: the materials exemplified for the lower electrode 64; electrode materials generally used in a semiconductor process, such as Al, Ta, Cr, and Cu; and combinations thereof Examples of the material of the piezoelectric film 66 include one or more types of perovskite oxide expressed by the following general expression (P).

$$A_a B_b O_3 \quad \text{General Expression (P)}$$

(where A represents A-site element(s), at least one type of element containing Pb; B represents B-site element(s), at least one type of element selected from the group consisting of Ti, Zr, V, Nb, Ta, Cr, Mo, W, Mn, Sc, Co, Cu, In, Sn, Ga, Zn, Cd, Fe, Ni, and lanthanide elements; and O represents an oxygen atom. In a standard case, a=1.0 and b=1.0, but these numerical values may be other than 1.0 within a range within which the perovskite structure can be maintained.)

If the piezoelectric film is formed according to the following vapor deposition method, the formed piezoelectric film can have such a composition that 1.0≤a and Pb is reliably contained, and can have even such a composition that 1.0<a and Pb is richly contained. There is not any particular upper limit to a, and the piezoelectric film having excellent piezoelectric performance can be obtained as long as 1.0≤a≤1.3.

The thicknesses of the lower electrode 64 and the upper electrode 68 are not particularly limited, and are, for example, about 200 nm. The thickness of the piezoelectric film 66 is not particularly limited, and is normally equal to or more than 1  μm, for example, 1 to 5 μm.

[Method of Forming the Piezoelectric Film]

Next, the method of forming the piezoelectric film is described. The piezoelectric film of the present invention can be formed according to a vapor deposition method using plasma, and the film forming conditions can be determined on the basis of the relation among: a film forming temperature Ts(° C.); Vs–Vf (V) that is a difference between a plasma potential Vs (V) in the plasma during film formation and a floating potential Vf (V); and characteristics of the film to be formed.

Examples of the applicable vapor deposition method include sputtering, ion-beam sputtering, ion plating, and plasma CVD. The characteristics of the film concerning the above-mentioned relation include a crystal structure of the film and/or a film composition, and the Young's modulus of the piezoelectric film can be changed by adjusting the film composition.

Figure 3A:
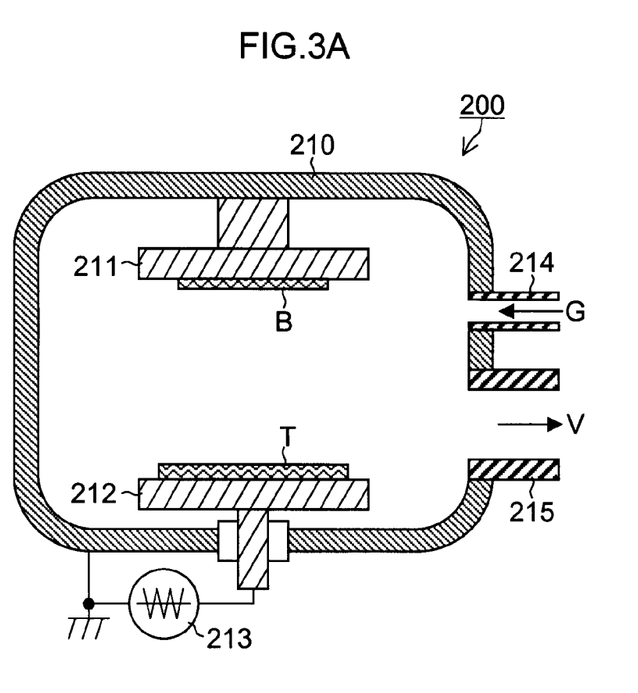
FIG. 3A is a cross-sectional view schematically illustrating an RF sputtering apparatus.
Figure 3B:
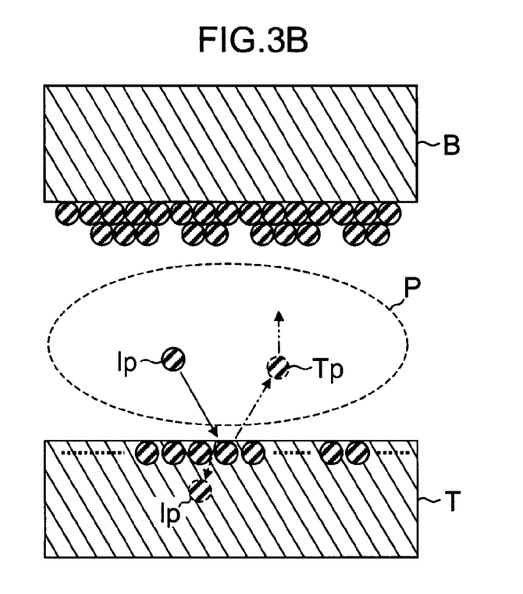
FIG. 3B is a view schematically illustrating a state during film formation.

With reference to FIGS. 3A and 3B, a configuration example of a film forming apparatus using plasma is described using a sputtering apparatus as an example. FIG. 3A is a cross-sectional view schematically illustrating an RF sputtering apparatus, and FIG. 3B is a view schematically illustrating a state during film formation.

A substrate B is set inside of the RF sputtering apparatus 200, and the RF sputtering apparatus 200 is roughly configured by a vacuum container 210 including: a heater 211 that can heat the set substrate B to a predetermined temperature; and a plasma electrode (cathode electrode) 212 that generates plasma. The heater 211 and the plasma electrode 212 are placed so as to face each other with an interval therebetween, and a target T having a composition corresponding to the composition of the film to be formed is set onto the plasma electrode 212. The plasma electrode 212 is connected to a high-frequency power source 213.

A gas inlet pipe 214 and a gas outlet pipe 215 are attached to the vacuum container 210. The gas inlet pipe 214 serves to introduce a gas G necessary for film formation into the vacuum container 210, and the gas outlet pipe 215 serves to discharge a waste gas V from the vacuum container 210. Ar, $Ar/O_2$ mixed gas, or other such gas is used as the gas G. As schematically illustrated in FIG. 3B, the gas G introduced into the vacuum container 210 is changed into plasma by electric discharge of the plasma electrode 212, so that positive ions Ip such as Ar ions are generated. The target T is sputtered by the generated positive ions Ip. A constituent element Tp of the target T sputtered by the positive ions Ip is emitted from the target to be deposited onto the substrate B in a neutral or ionized state. In FIG. 3B, reference character P designates a plasma space.

The potential of the plasma space P is equal to the plasma potential Vs (V). Normally, the substrate B is an insulator, and is electrically insulated from a ground. Accordingly, the substrate B is in a floating state, and the potential thereof is equal to the floating potential Vf (V). The target constituent element Tp existing between the target T and the substrate B collides against the substrate B during film formation while having kinetic energy corresponding to an accelerating voltage of the potential difference Vs–Vf between the potential of the plasma space P and the potential of the substrate B.

The plasma potential Vs and the floating potential Vf can be measured using a Langmuir probe. As the voltage of the probe is made higher than the floating potential Vf, an ion current gradually decreases, and eventually only an electron current reaches the probe. The voltage at this border is the plasma potential Vs. Vs–Vf can be changed by, for example, providing a ground between the substrate and the target.

In the vapor deposition method using plasma, conceivable factors that affect the characteristics of the film to be formed include: a film forming temperature; the type of the substrate; if any other film has already been formed on the substrate, the composition of this underlying film; surface energy of the substrate; a film forming pressure; the amount of oxygen contained in an atmosphere gas; an input electrode; the distance between the substrate and the target; the temperature and density of electrons in the plasma; and the concentration and lifetime of active species in the plasma.

In addition to the above-mentioned vapor deposition method using plasma, the piezoelectric film of the present invention can be similarly formed according to: a gas phase method such as a metal-organic chemical vapor deposition (MOCVD) method and a pulsed laser deposition (PLD) method; a liquid phase method such as a sol-gel method and a metal-organic decomposition method; and an aerosol deposition method. Alternatively, the piezoelectric film can also be formed by directly joining bulk ceramics and then polishing the bulk ceramics to a desired film thickness. Owing to the difference in coefficient of thermal expansion between the substrate and the piezoelectric film, a compressive stress can be applied to the piezoelectric film by making the film forming temperature high, but the present invention is not limited thereto. The method of forming the piezoelectric film is not particularly limited as long as a compressive stress can be applied as an internal stress to the piezoelectric film.

[Performance of the Piezoelectric Film]

In general, the tensile strength of the ceramics is smaller than the compressive strength thereof. For example, in the case of PZT, the tensile strength is one digit smaller than the compressive strength (see Piezoelectric Ceramics Technical Handbook, Table 7.9.2; Fuji Ceramics Corporation). Accordingly, a maximum value Vm of the speed of the resonant transducer depends on a tensile strength Tm, and can be obtained by the following expression.

$$Vm = \frac{Tm}{\rho \cdot c} \quad \text{[Expression 1]}$$

where $\rho$ represents the density of the vibrator, and c represents the sonic speed of the vibrator.

Because the tensile strength refers to the strength at which the ceramics break, in actuality, the ceramics start to generate heat at a speed lower than the maximum value Vm, and the speed of the resonant transducer is reduced by energy loss caused by the heat generation. Hence, the limit value of the speed of the resonant transducer is smaller than Vm. Accordingly, the apparent tensile strength of the piezoelectric film can be increased by applying a bias of a compressive stress to the piezoelectric film at the initial stage.

The internal stress of the piezoelectric film results from: a thermal stress due to the difference in coefficient of thermal expansion between the substrate and the piezoelectric film during the formation of the piezoelectric film; and the growth process of the piezoelectric film. The present invention focuses on the internal stress resulting from the thermal stress, and a compressive stress is applied to the piezoelectric film.

For example, the coefficient of thermal expansion of Ti-6Al-4V is 8.8 ppm/° C., and the coefficient of thermal expansion of a PZT thin film is 6.7 ppm/° C. Accordingly, when the temperature is returned from the film forming temperature to room temperature, an amount of distortion corresponding to the film forming temperature occurs, and hence a compressive stress can be applied to the piezoelectric film. As a result, when the resonant transducer is vibrated, a tensile strength higher than that in the conventional case can be applied, and hence a high vibration speed can be achieved.

The internal stress of the piezoelectric film is preferably a compressive stress equal to or higher than 100 MPa and more preferably a compressive stress equal to or higher than 300 MPa.

Note that the internal stress thereof is obtained according to the following expression of Stoney on the basis of a warpage amount R of the resonant transducer using a laser interferometer.

Expression of Stoney [Expression 2]

$$\sigma = \frac{Et^2}{6t_{cr}(1-v_s)R}$$

where E and $v_s$ respectively represent the Young's modulus and Poisson's ratio of the substrate, and $t_{cr}$ and t respectively represent the thicknesses of the piezoelectric film and the substrate.

[Ultrasonic Treatment Tool]

Figure 4:
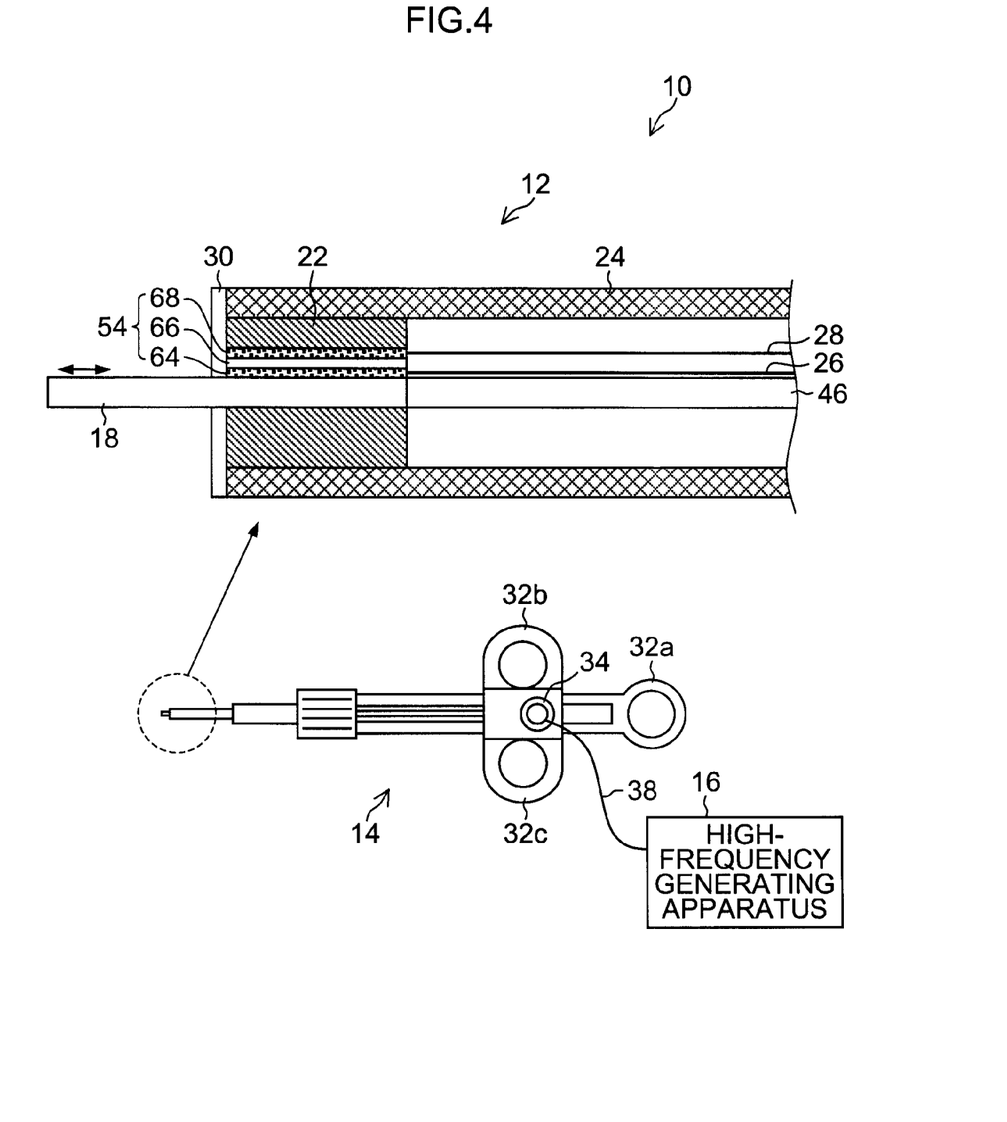
FIG. 4 is an overall configuration view illustrating an ultrasonic treatment tool.

Next, an example of the ultrasonic treatment tool including the resonant transducer according to the present invention is described. FIG. 4 is an overall configuration view illustrating, as the example of the ultrasonic treatment tool, an ultrasonic treatment tool 10 including an ultrasonic knife. The ultrasonic treatment tool 10 includes: a knife part 12 that functions as an ultrasonic knife (scalpel) such as a needle-like knife and a knife for peripheral incision and mucosal dissection (hereinafter, also referred to as "incision/dissection knife") in ESD treatment; an operation part main body 14 that is operated by an operator such that the knife part 12 functions as the ultrasonic knife; and a high-frequency generating apparatus 16 that supplies a high-frequency voltage to the knife part 12.

The knife part 12 includes a blade part (treating part) 18, the piezoelectric element 54, a blade fixing portion 22, a flexible sheath (connection part) 24, a first electrode (ground potential) 26, a second electrode 28, a resin sealing material 30, and a flexible code 46.

In addition, the operation part main body 14 includes a ring 32a, a ring 32b, and a ring 32c for operating the blade part 18 and a connector 34 that is a terminal for connecting with the high-frequency generating apparatus 16.

Note that the connector 34 of the operation part main body 14 is electrically connected to the high-frequency generating apparatus 16 by a high-frequency voltage code 38.

The blade part 18 of the knife part 12 functions as the incision/dissection knife used for peripheral incision, entire-circumferential incision (cut), submucosal dissection, and other such operations in ESD treatment. The blade part 18 can be vibrated by the vibration of the piezoelectric element 54.

The piezoelectric element 54 is expanded/contracted by increasing/decreasing an electric field intensity applied to the piezoelectric element 54, whereby the blade part 18 is ultrasonically vibrated in the direction indicated by an arrow in FIG. 4, thus enabling the incision.

The blade fixing portion 22 is fixed to the inside of the leading end of the sheath 24, and has a function of supporting the blade part 18 such that the blade part 18 can reciprocate (go forward and backward). That is, when the blade part 18 protrudes and retracts from the leading end of the sheath 24, the blade fixing portion 22 supports the blade part 18 such that the blade part 18 can go forward and backward with respect to the sheath 24.

The sheath 24 is made of a flexible insulating material, and physically and electrically protects the blade part 18, the piezoelectric element 54, the first electrode 26, and the second electrode 28.

The first electrode 26 and the second electrode 28 serve to supply a high-frequency voltage to the piezoelectric element 54, are made of a conductive material, and are coupled to the rings 32b and 32c.

The resin sealing material 30 is provided for sealing the biological body side of the sheath 24. In the present invention, the piezoelectric element 54 can be provided in a portion to be inserted into a body, and hence it is preferable to cover the piezoelectric element 54 with a resin in order to prevent an electrical shock. In addition, lead can be used as the material of the piezoelectric film 66, and hence it is preferable to cover the piezoelectric element 54 with a resin. The use of a resin as the sealing material of the sheath 24 can reduce an influence of the resonant frequency during the driving of the blade part 18.

Next, the configuration and action of the operation part main body 14 is described.

An operator inserts his/her thumb into the ring 32a of the operation part main body 14 and his/her index finger and middle finger into the rings 32b and 32c as sliders for operation. In this state, if the operator slides the sliders for operation with respect to the operation part main body 14, this sliding enables the blade part 18 to go forward and backward (reciprocate) with respect to the sheath 24 via the flexible code 46 coupled to the sliders for operation.

The high-frequency voltage code 38 from the high-frequency generating apparatus 16 is connected to the connector 34, and the first electrode 26 is electrically connected to the second electrode 28. Hence, the high-frequency voltage from the high-frequency generating apparatus 16 is applied to both the first electrode 26 and the second electrode 28. Then, the blade part 18 is ultrasonically vibrated by the vibration of the piezoelectric element 54, and thus can function as the incision/dissection knife.

The diameter of a forceps port of a treatment tool (endoscope) including the above-mentioned ultrasonic knife is about 3 mm. If the treating part is provided with the vibration amplifying portion (horn shape), the speed of vibration from the driving portion can be increased. Unfortunately, as the increase rate of the horn is larger, the size of the treating part (vibrating portion) needs to be smaller because the applicable diameter is limited. If the treating part is thus smaller, the amount of work necessary for the treatment is larger, resulting in an unfavorable increase in operation time. An ultrasonic knife used at present has a leading end diameter of about 1 mm and a transformation ratio of about 3. In the case of an exponential horn, the transformation ratio can be obtained by the diameter ratio of the vibrating portion to the treating part, and hence it is preferable to set the transformation ratio to be equal to or less than 2. The vibration speed required for an ultrasonic scalpel is equal to or more than 7 m/s. Hence, in order to obtain a transformation ratio equal to or less than 2, it is preferable to use a rectangular configuration without a transformation ratio and set the vibration speed thereof to be equal to or more than 3.5 m/s.

Note that the resonant transducer according to the present invention is not limitatively applied to the above-mentioned ultrasonic knife, but can also be applied to various actuators, resonators, sensors, oscillators, and any other suitable devices.

EXAMPLES

A resonant transducer having such a rectangular configuration as illustrated in FIG. 1A was produced using a substrate of a Ti alloy, that is, Ti-6Al-4V having a tensile strength of 800 MPa. The vibrating portion was fixed by the fixing portion to the supporting portion. The thickness of the substrate was 0.3 mm.

A first layer TiW having a thickness of 50 nm and a second layer Ir having a thickness of 150 nm were formed on the substrate by sputtering as the lower electrode. A lead zirconate titanate (PZT) film was formed on the lower electrode by sputtering under the respective conditions of a film forming temperature of 550° C. (Example 1), a film forming temperature of 600° C. (Example 2), and a film forming temperature of 650° C. (Example 3). The thickness of the piezoelectric film was 4 μm. Next, a first layer TiW having a thickness of 50 nm and a second layer Pt having a thickness of 150 nm were formed thereon by sputtering as the upper electrode. The film forming conditions were set as follows:

Film forming apparatus: Rf sputtering apparatus;
Target: $Pb_{1.3}((Zr_{0.52}Ti_{0.48})_{0.88}Nb_{0.12})O_3$ sintered body (amount of Nb contained in B-site: 12 mol %);
Substrate temperature: 450° C.;
Distance between substrate and target: 60 mm;
Film forming pressure: 0.29 Pa; and
Film forming gas: $Ar/O_2$=97.5/2.5 (molar ratio).

The compressive stress applied to the resonant transducer thus produced was obtained. In addition, a voltage of 0.7 V was applied to the Ti substrate electrically connected to the lower electrode and an electrode pad electrically connected to the upper electrode, whereby the vibrating portion was vibrated. Then, the vibration speed of a side surface of the resonant transducer was measured using a laser Doppler vibrometer, so that the resonant frequency was obtained. With regard to the obtained resonant frequency, the vibration speed was obtained by changing the drive voltage. The results are shown in Table 1 and FIGS. 5 and 6. Note that, for all the piezoelectric films according to Examples 1 to 3, the degree of orientation in the (100) direction was equal to or more than 80%, and the piezoelectric constant $d_{31}$ was 200 to 250 pm/V.

TABLE 1

|  | Film forming temperature | Compressive stress | Resonant frequency | Maximum speed |
| --- | --- | --- | --- | --- |
| Example 1 | 550° C. | 100 MPs | 291.03 Hz | 3.7 m/s |
| Example 2 | 600° C. | 220 MPs | 293.32 Hz | 5.2 m/s |
| Example 3 | 650° C. | 300 MPs | 292.68 Hz | 7.8 m/s |

Figure 5:
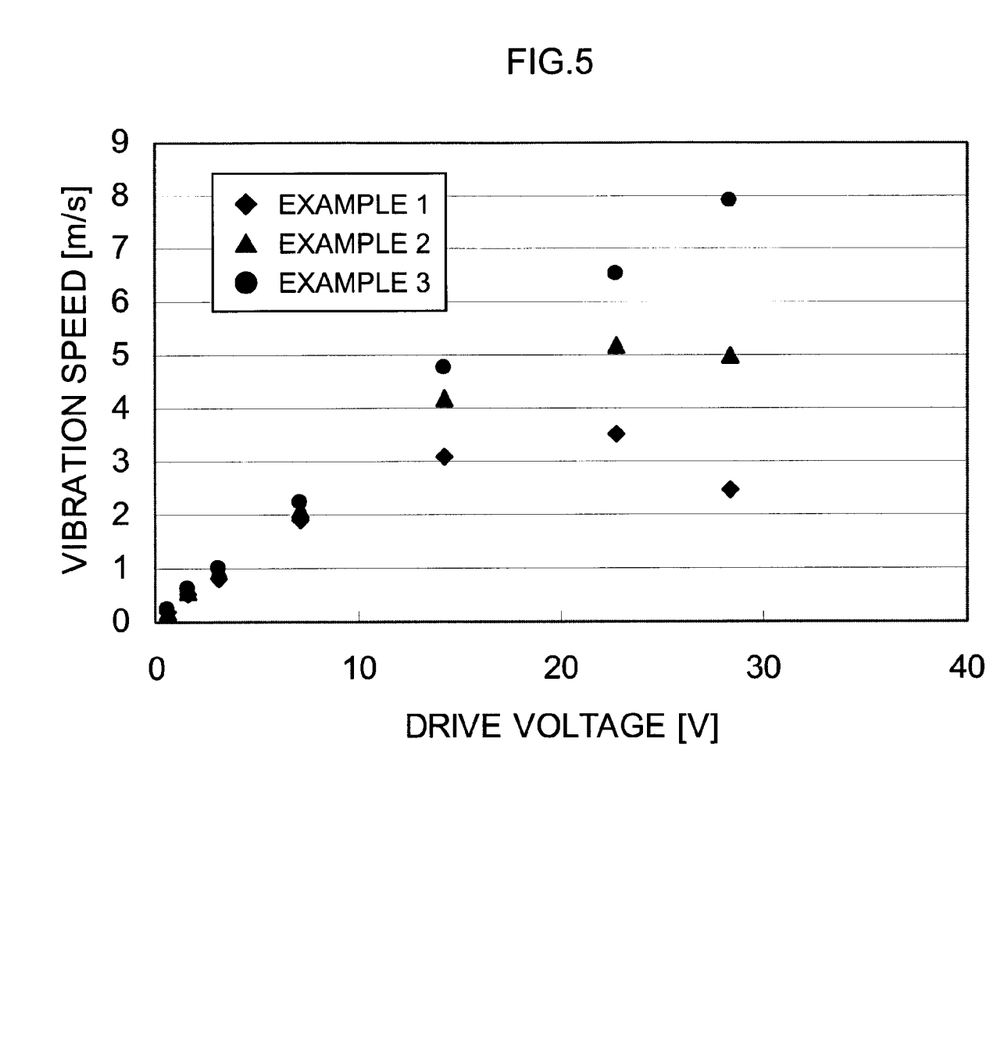
FIG. 5 is a graph showing the relation between a drive voltage and a vibration speed according to Examples.

With reference to FIG. 5, for all the samples according to Examples 1 to 3, substantially the same vibration speed could be obtained in a region of a voltage equal to or less than 10 V.

In Example 1, a peak vibration speed of 3.7 m/s could be obtained at 22 V. As the voltage was further increased, however, the speed decreased at 28 V. The reason for this is considered to be as follows. Because the compressive stress is small, when the vibration speed becomes equal to or more than 3 m/s, heat starts to be generated due to a tensile stress during vibration, resulting in an increase in energy loss. As the voltage is higher, the input energy is larger. Hence, the amount of generated heat is also larger, and the vibration speed starts to decrease after a given peak voltage.

In Example 2, a maximum vibration speed of 5.2 m/s could be obtained at 22 V. Because the compressive stress in Example 2 was larger than that in Example 1, the speed higher than that in Example 1 could be obtained. Even in Example 2, however, when a voltage equal to or more than 22 V was applied, heat started to be generated due to a tensile stress during vibration, and the speed decreased.

In Example 3, a maximum vibration speed of 7.8 m/s could be obtained at 28 V. Even when the voltage was increased, the speed did not decrease, and there was a proportional relationship between the drive voltage and the vibration speed.

Figure 6:
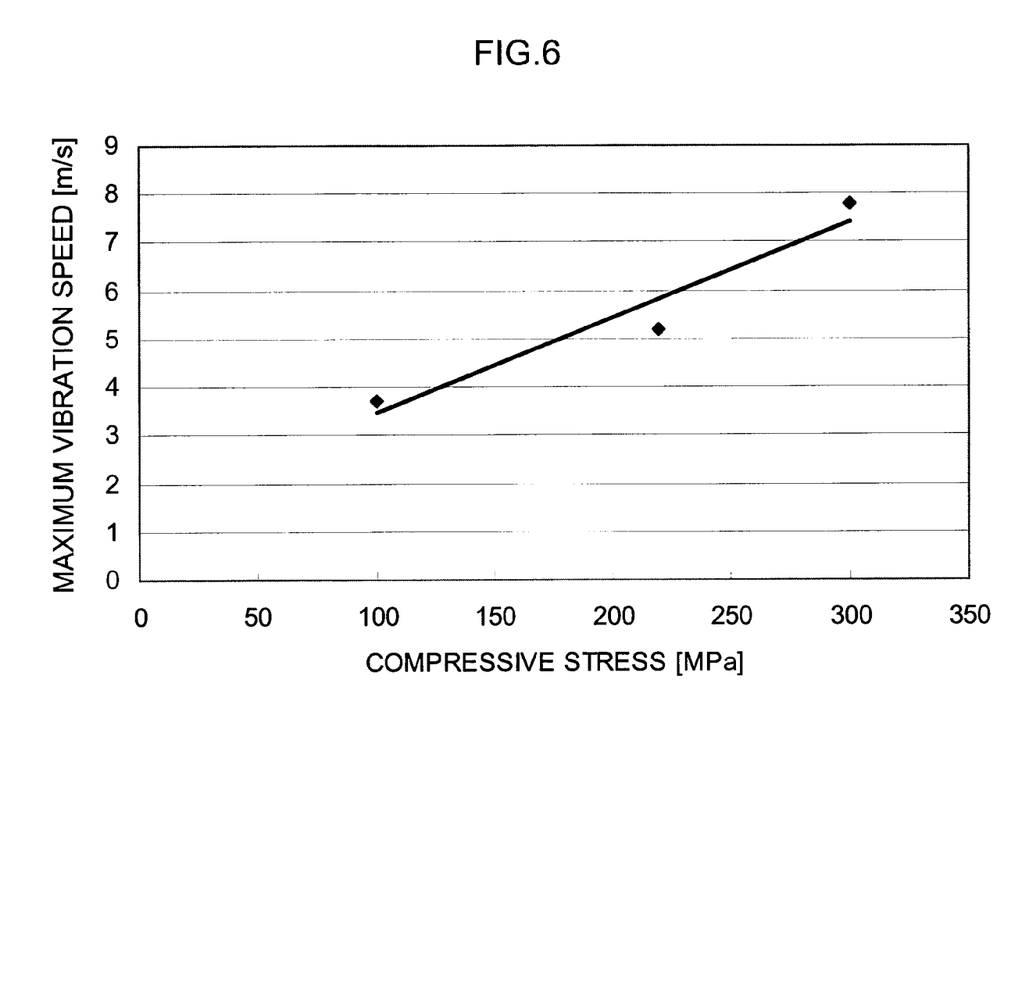
FIG. 6 is a graph showing the relation between a compressive stress and a maximum vibration speed according to Examples.

FIG. 6 is a graph showing the relation between a compressive stress and a maximum vibration speed. There was found a linear relationship between the compressive stress and the maximum vibration speed, and y=0.02x+1.46 was obtained by an approximate curve.

Considering the fact that the vibration speed required for an ultrasonic knife is equal to or more than 7 m/s, the vibration speed needs to equal to or more than 3.5 m/s in the case of the rectangular configuration (the configuration without a horn). Accordingly, it is necessary to set the compressive stress to be equal to or more than 100 MPa, and a resonant transducer having a transformation ratio equal to or less than 2.0 can be obtained using the samples according to Examples 1 to 3.

In addition, if the compressive stress applied to the piezoelectric film is set to be equal to or more than 300 MPa as in Example 3, the vibration speed can be equal to or more than 7 m/s. Hence, the function as an ultrasonic knife can be achieved without providing the horn part (vibration amplifying portion), and the size of the treating part can be larger. In addition, in the case where the driving portion is formed in a portion to be inserted into a body, it is preferable to suppress the drive voltage to be low, that is, equal to or less than 30 V. In Example 3, it was found as shown in FIG. 5 that the vibration speed was enhanced by increasing the drive voltage in the range in which the drive voltage was equal to or less than 30 V.

For a comparative example, "Enhancement of Vibration Amplitude of Micro Ultrasonic Scalpel using PZT Film", Minoru KUROSAWA and Takeshi SASANUMA, Technical Report of The Institute of Electronics, Information and Communication Engineers (IEICE), US2009-109(213)31, which is cited as the related art, describes that, in the case where a piezoelectric element is formed on one surface of a substrate, the vibration speed is about 2 m/s at a drive voltage of 20 V (see FIG. 11 of this technical report). The piezoelectric film is formed by hydrothermal synthesis, and hence it is considered that an internal stress is not applied to the piezoelectric film. As is apparent from this technical report, a resonant transducer having a low compressive stress cannot achieve a sufficient vibration speed.

What is claimed is:

1. A resonant transducer comprising:
a vibration plate; and
a piezoelectric element including a piezoelectric film and an upper electrode that are laminated on the vibration plate, wherein
a compressive stress is applied to the piezoelectric film,
the vibration plate vibrates in an expanding/contracting manner in a direction parallel to a surface on which the piezoelectric element is formed, and
the vibrating plate is supported only in a surface perpendicular to a vibration direction of the vibrating plate and parallel to a lamination direction of the vibration plate and the piezoelectric element.

2. The resonant transducer according to claim 1, wherein the piezoelectric film has a film thickness that is equal to or more than 1 μm and equal to or less than 5 μm.

3. The resonant transducer according to claim 2, wherein an internal stress of the piezoelectric film is a compressive stress equal to or more than 100 MPa.

4. The resonant transducer according to claim 3, wherein an internal stress of the piezoelectric film is a compressive stress equal to or more than 300 MPa.

5. The resonant transducer according to claim 1, wherein the vibrating plate has a coefficient of thermal expansion larger than a coefficient of thermal expansion of the piezoelectric film.

6. An ultrasonic treatment tool comprising the resonant transducer according to claim 1.

* * * * *